United States Patent [19]
Kanesaka et al.

[11] Patent Number: 5,776,183
[45] Date of Patent: Jul. 7, 1998

[54] EXPANDABLE STENT

[76] Inventors: Nozomu Kanesaka, 36 Cathy Rd.;
George A. Tashji, 24 Cathy Rd., both
of Hillsdale, N.J. 07642

[21] Appl. No.: 702,167

[22] Filed: Aug. 23, 1996

[51] Int. Cl.⁶ .................................................. A61F 2/06
[52] U.S. Cl. .................. 623/1; 623/12; 623/11;
606/194; 606/195; 606/198
[58] Field of Search .......................... 623/1, 11, 12;
606/194–200, 157–158; 600/36

[56] References Cited

U.S. PATENT DOCUMENTS

| | | | |
|---|---|---|---|
| 5,059,166 | 10/1991 | Fischell et al. | 600/3 |
| 5,135,536 | 8/1992 | Hillstead | 606/195 |
| 5,139,480 | 8/1992 | Hickle et al. | 612/12 |
| 5,344,426 | 9/1994 | Lau et al. | 606/198 |
| 5,441,515 | 8/1995 | Khosravi et al. | 606/194 |
| 5,449,373 | 9/1995 | Pinchasik et al. | 606/198 |
| 5,496,365 | 3/1996 | Sgro | 623/1 |
| 5,527,354 | 6/1996 | Fontaine et al. | 623/1 |
| 5,540,713 | 7/1996 | Schnepp-Pesch et al. | 606/198 |
| 5,554,181 | 9/1996 | Das | 623/1 |
| 5,562,697 | 10/1996 | Christiansen | 606/191 |
| 5,569,295 | 10/1996 | Lam | 606/198 |
| 5,575,816 | 11/1996 | Rudnick et al. | 623/1 |

FOREIGN PATENT DOCUMENTS

| | | | |
|---|---|---|---|
| 540290 | 5/1993 | WIPO | 623/1 |
| 94/17754 | 8/1994 | WIPO | 623/1 |
| 95/03010 | 2/1995 | WIPO | 623/1 |

*Primary Examiner*—John G. Weiss
*Assistant Examiner*—Francis K. Cuddihy
*Attorney, Agent, or Firm*—Kanesaka & Takeuchi

[57] ABSTRACT

An expandable tubular reinforcing member of the invention is used for a body lumen. The reinforcing member is basically formed of a plurality of rows of expandable joint members and a plurality of rows of flexible elongated members. The joint members in one row are arranged in a circular form and are spaced apart from each other. The elongated members in one row are arranged in a circular form, and each flexible elongated member extends diagonally to a central axis of the reinforcing member and connects two of the joint members situated in adjacent two rows. When a radial force is applied from an inside of the reinforcing member, the elongated members are bent relative to the joint members to have a larger diameter.

18 Claims, 2 Drawing Sheets

EXPANDABLE STENT

BACKGROUND OF THE INVENTION AND RELATED ART STATEMENT

The invention relates to an expandable endoprosthesis device, generally called a stent, which is implanted into a patient's body lumen, such as a blood vessel, to maintain patency thereof. The stent is very useful in the treatment of atherosclerotic stenosis in the blood vessels.

The stent is, generally, a tubular shaped device which functions to support a part of a blood vessel or another anatomical lumen from the inside thereof, and is particularly suitable for supporting and holding a dissected arterial lining which may occlude a fluid passageway by collapse thereof. "Stent" here is defined as a prosthetic member used for reinforcing the blood vessel.

Various methods have been used to deliver and implant stents. In one of the methods frequently used for delivering a stent to a desired inter lumenal location, an expandable stent is mounted on an expandable member, such as a balloon, provided on a distal end of an intravascular catheter, and the catheter is advanced to the desired location within the patient's body lumen. Then, the balloon on the catheter is inflated to expand the stent therearound to have a permanent expanded condition, and the balloon is deflated for removing the catheter from the stent.

Therefore, advantages of the method of strengthening the blood vessel by the stent over the conventional vascular surgery include obviating the surgical exposing, and incising, removing, replacing or bypassing a defective blood vessel required in the conventional vascular surgery.

The stents in the prior art can be categorized as a wire type stent or a coil stent and a tube stent. Further details of prior art stents can be found in U.S. Pat. No. 3,868,956 (Alfidi et al.); U.S. Pat. No. 4,512,338 (Balko et al.); U.S. Pat. No. 4,553,545 (Masass et al.); U.S. Pat. No. 4,733,665 (Palmaz); U.S. Pat. No. 4,762,120 (Rosenbluth); U.S. Pat. No. 4,800,882 (Gianturco); U.S. Pat. No. 4,856,516 (Hillstead); U.S. Pat. No. 4,886,062 (Wiktor) and U.S. Pat. No. 5,421,955 (Lau et al.).

When the stent is expanded as described above, it is important to maintain the stent in the expanded condition so that the body lumen expanded by the stent can be remained open. The prior wire type stent or the coil sent is made by simply bending a wire having a flexibility so that the wire stent is easily expanded and shrunk. Therefore, the wire type stent, had difficulties in maintaining the radially expanded condition for holding the body lumen open.

On the other hand, when the stent is delivered into the desirable site in the tortuous body lumen, it is also important that the stent is flexible and is bent easily to thereby facilitate the delivery of the stent in the narrow and meandering body lumen such as a blood vessel. Also, in view of expanding the stent in the body lumen for the treatment, it is important to expand the stent quickly so that the balloon catheter can be removed from the patient's body as quickly as possible.

In the tube type stent of the prior art, the tube stent has enough stiffness to maintain its expanded condition for holding the body lumen open at the desirable location. However, since the tube stent is not flexible as in the wire type stent, it is difficult to deliver the tube stent in the tortuous lumen to locate the stent in the desirable site.

Furthermore, when the radial force by the expandable member, such as a balloon, is applied from the inside of the stent, the forces applied at both ends of the stent are greater than the force applied to an inner portion of the stent. Therefore, both ends of the stent may be excessively expanded as compared to the inner portion of the stent, so that the body lumen can not be equally expanded by such a stent.

Accordingly, one object of the invention is to provide a stent, which has a high degree of flexibility and expandability for advancing through passageways.

Another object of the invention is to provide a stent as stated above, which is readily and equally expandable throughout the entire length thereof.

A further object of the invention is to provide a stent as stated above, which has a mechanical strength to hold the body lumen open equally, as well.

Further objects and advantages thereof will be apparent from the following description of the invention.

SUMMARY OF THE INVENTION

To achieve the aforementioned objects of the invention, a stent of the invention is formed of an expandable tubular reinforcing member used for a body lumen, and includes a plurality of rows of expandable joint members and a plurality of rows of flexible elongated members. Each row of the joint members is spaced for a predetermined distance away from each other along the central axis of the reinforcing member, and is formed of the joint members spaced apart from each other to form a circular shape around the central axis with a first diameter.

Each row of the elongated members is situated between adjacent two rows of the joint members. The elongated members extend diagonally to a central axis of the reinforcing member. Therefore, when a radial force is applied from an inside of the reinforcing member, the elongated members are bent relative to the joint members to thereby allow the tubular reinforcing member to have a second diameter larger than the first diameter.

In addition, since the elongated members are diagonally arranged and connected between the joint members spaced away from each other, the stent has enough flexibility to facilitate the delivery of the stent into the desirable site in the meandering body lumen.

The expandable tubular reinforcing member may include two rows of end portions fixed to the rows of the joint members. Each row of the end portions is connected to a row of the joint members located at each longitudinal end of the reinforcing member, and is formed of a plurality of struts situated parallel to the central axis and connected to the joint members and a plurality of connecting portions. Each connecting portion connects a pair of struts situated adjacent to each other. In particular, each connecting portion has a thickness less than that of each strut. When the reinforcing member is expanded, each connecting portion is bent. Also, each strut has a length shorter than a length of each elongated member. Therefore, when the reinforcing member is expanded, the struts are equally bent at both ends at the same time.

In the invention, since the stent is provided with the end portions formed of the struts parallel to the control axis of the stent and the connecting portions, the ends of the stent can be prevented from excessive expansion to equalize the expansion of the stent throughout the entire length thereof even though the expanding forces at the ends of the stent are greater than the force at the inner portion of the stent.

Each joint member is preferably formed of two side portions and one middle portion for joining the two side portions. Two elongated members are connected to one side portion of one joint member in one row of the joint members and are connected to two side portions of the joint members in the adjacent row of the joint members. The middle portion may be connected to the respective ends of the two side portions to have an open side in the joint member. The open sides in one row of the joint members are oriented in the same direction, and the open sides in the adjacent two rows are directed in the opposite directions.

Also, the elongated members may be formed of first and second elongated members alternately arranged to each other in one row of the elongated members. Each first elongated member is connected to the side portion near the open side in the joint member, and each second elongated member is connected to the side portion near the middle portion. When the reinforcing member is expanded, the first elongated members are bent first, and then the second elongated members are bent.

Preferably, the elongated members are integrally formed with the joint members and the end portions.

DETAILED DESCRIPTION OF A PREFERRED EMBODIMENT

Hereinafter, an embodiment of the present invention is explained by referring to the attached drawings.

Figure 1:
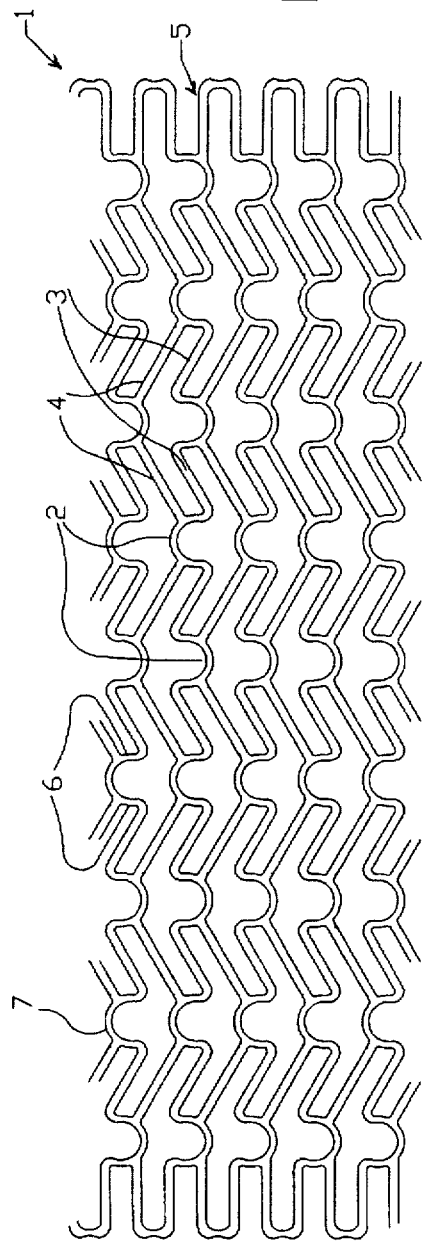
FIG. 1 is a plan view of an expandable stent of the present invention, wherein the stent is cut along a longitudinal direction and is opened to show a flat condition.

In the embodiment of the present invention as shown in FIGS. 1 through 6, a stent 1 situated in a human body lumen, such as a blood vessel, is formed of a plurality of flex joints 2, a plurality of elongated members 3, 4 connected to the flex joints 2, and a plurality of end portions 5. As shown in FIG. 1, i.e. a plan view cut into a flat form, plural rows of the flex joints 2 are disposed to be spaced away from each other along a longitudinal direction or central axis of the stent formed in a round shape. In each row, a plurality of flex joints is disposed to be spaced away from each other, and first and second elongated members 3, 4 connected in one joint 2 are connected to two flex joints 2 in the adjacent row, and extend diagonally to the central axis of the stent.

Figure 2:
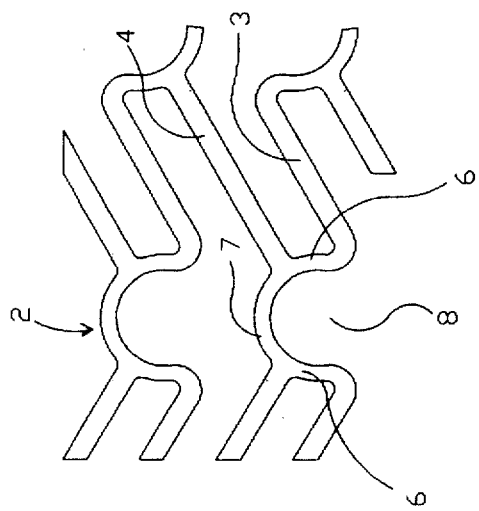
FIG. 2 is an enlarged plan view of a part of the embodiment shown in FIG. 1.

As shown in the magnified partial view of the stent of FIG. 2, the flex joint 2 has a semicircular shape and is formed of a pair of side portions 6, and a middle portion 7, wherein the side portions 6 are connected to both ends of the middle portion 7. The middle portion 7 and the two side portions 6 define an open side 8. Also, in the adjacent two rows, the flex joints 2 orient in opposite directions. For example, the open sides 8 of one row of the flex joints 2 orient upwardly, while the open sides 8 of another row situated next to that row orient downwardly.

As shown in FIG. 1, each first elongated member 3 connects between the respective side portions 6 near the open sides 8 in the two adjacent rows of the flex joints 2, and each second elongated member 4 connects between the respective side portions 6 near the middle portions 7 in the adjacent two rows.

Figure 3:
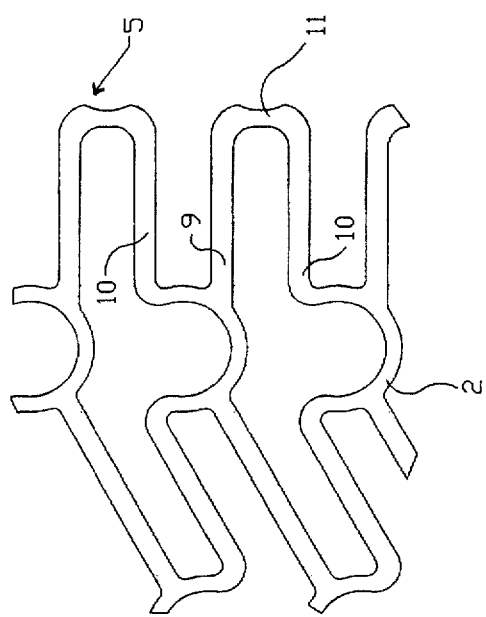
FIG. 3 is an enlarged plan view of an end portion of the embodiment shown in FIG. 1.

As shown in FIG. 3, each end portion 5 is formed of a pair of struts 9, 10 arranged parallel to each other, and a connecting part 11. The connecting part 11 connects one strut 9 in one end portion 5 and one strut 10 in another end portion 5. Thus, the two flex joints 2 situated adjacent to each other are connected together by one end portion 5, respectively. The thickness of the connecting part 11 is thinner than the thickness of the struts 9, 10.

Figure 4:
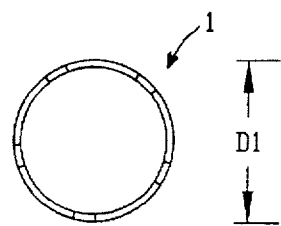
FIG. 4 is a front view of the stent before it is expanded.
Figure 5:
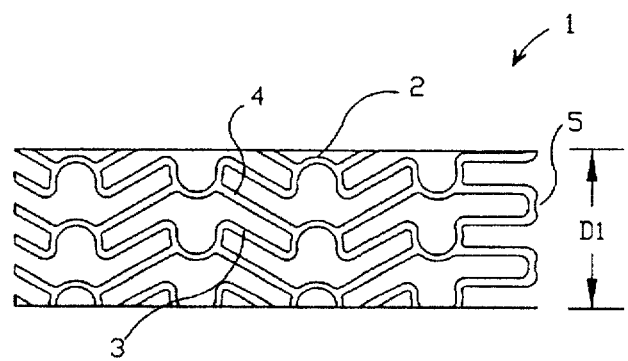
FIG. 5 is a side view of the stent before it is expanded.

In the invention, the rows of the flex joints 2 and the elongated members 3, 4 are disposed perpendicularly to the central axis of the stent 1. The flex joints 2 situated in adjacent rows orient in the opposite directions, while the first and second elongated members 3, 4 located in the adjacent rows orient or incline in the opposite directions. Namely, the first and second elongated members 3, 4 in one row incline in one direction on the outer surface of the stent, and the first and second elongated members in the adjacent row incline in the opposite direction, on the outer surface or the stent. Also, the rows of the end portions 5 are located at longitudinal ends of the stent 1, wherein the struts 9, 10 orient parallel to the central axis. When the stent is formed, the stent 1 has a first diameter $D_1$, as shown in FIGS. 4 and 5.

The stent is preferably formed by etching. Namely, a pattern of the flex joints 2, elongated members 3, 4 and the end portions 5 are coated on a cylindrical metal member, which is etched in an acid liquid. Then, uncoated portions are removed. Other suitable methods may be used. For example, the stent can be formed by laser cutting.

When the stent 1 is used in the body lumen, such as a blood vessel, the stent 1 is delivered to the desired location in the body lumen by mounting it on an expandable member, such as a balloon, of a delivery catheter. When the stent 1 is delivered, since the elongated members 3, 4 diagonally extend between the flex joints 2, the elongated members 3, 4 can be bent easily along the body lumen. Accordingly, a stent catheter assembly is successfully pushed into the implantation site.

Figure 6:
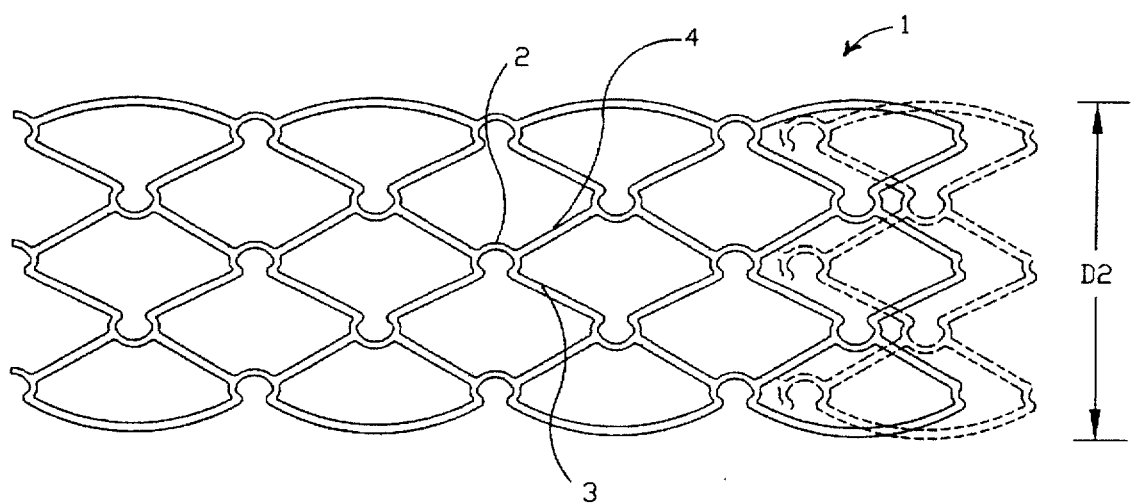
FIG. 6 is a side view of the stent after it is expanded.

Then, when the expandable member, such as the balloon, is inflated for radially applying the force inside the stent 1, the stent 1 is expanded to have a second diameter $D_2$, as shown in FIG. 6, which is larger than the first diameter $D_1$. When the stent 1 is expanded, the first elongated members 3 are bent outwardly to expand the stent 1 first, and after the first elongated members 3 are bent, the second elongated members 4 are bent to further expand the stent 1.

The struts 9, 10 in the end portion 5 of the stent 1 have lengths shorter than that of the respective elongated members and extend parallel to the central axis of the stent. Also, the struts 9, 10 are connected to the connecting part 11 and the flex joints 2. Thus, when the expandable member is inflated, the struts 9, 10 are bent equally at the same time.

Since the first and second elongated members 3, 4 are arranged diagonally to the central axis of the stent 1, the first and second elongate members are easily expanded as compared to the struts 9, 10 arranged parallel to the central axis of the stent 1. Since the force applied to the ends of the stent is greater than the force applied at the middle portion of the stent 1, the stent 1 can be expanded equally throughout the entire length thereof.

Also, the cylindrical design of the stent 1 may allow the plastic deformation of the metal (except for NiTi) when the stent is expanded. This plastic deformation can maintain the stent in its expanded position and resist collapsing in the body. With super elastic NiTi alloys, the expansion occurs when the stress of compression is removed so as to allow the phase transformation from austenite back to martensite as a result of the expansion of the stent 1.

The stent is formed of stainless steel, or may be formed of a NiTi alloy. Alteratively, the stent may be made of a radioactive material or irradiated with a radioactive isotope. The radioactive isotope may be a beta particle emitting radioisotope. By using the stent made of the radioactive material, cancer cells in and around the stent can be deactivated or killed.

Alternatively, the stent may be coated with an anticoagulating medication substance, such as heparin, and/or bio-absorbable material. Accordingly, when the stent is used in the blood vessel, blood clotting can be prevented.

Also, the stent may have pores or dents to absorb or retain a drug therein for slowly releasing the same. Thus, when the stent with a drug is implanted in the body lumen, the drug can be slowly released in the body lumen.

Preferably, as shown in FIG. 3, the thickness of the flex joint 2 is thinner than that of the elongated member to be bendable. The spacing of the flex joint 2, the respective length of the elongated members 3, 4, the thickness of the connecting part 11 and the like can be variable to allow the stent to have flexibility in various directions along its length without compromising the radial support for preventing the body lumen from collapsing. Therefore, the stent of the invention can support any dissection and flap in the body lumen.

Also, the number and location of the flex joints and the elongated members can be varied in order to develop the desired longitudinal flexibility in the stent structure both in the unexpanded stage and in the expanded stage.

While the invention has been explained with reference to the specific embodiments of the invention, the explanation is illustrative and the invention is limited only by the appended claims.

What is claimed is:

1. An expandable tubular reinforcing member used for a body lumen comprising,
a plurality of rows of joint members, each of the rows being spaced for a predetermined distance away from each other along a central longitudinal axis of the reinforcing member, each row being formed of a plurality of said joint members spaced apart from each other and arranged circularly around the central axis with a first diameter, and
a plurality of rows of flexible elongated members, each of the rows being situated between adjacent two rows of the joint members and arranged circularly around the central axis, said elongated members in each of the rows being inclined substantially in a same direction and diagonally with an acute angle with respect to a line on a surface of the reinforcing member parallel to the central axis of the reinforcing member, each of said elongated members connecting two of the joint members situated in adjacent two rows of the joint members, said elongated members in two rows sandwiching one row of the joining members to be connected together and being arranged substantially symmetrically relative to said one row of the joint members situated therebetween so that when a radial force is applied from an inside of the reinforcing member, the elongated members are pivoted relative to the joint members to thereby allow the reinforcing member to have a second diameter larger than the first diameter.

2. An expandable tubular reinforcing member according to claim 1, further comprising two rows of end portions disposed parallel to the rows of the joint members, each row of the end portions being connected to a row of the joint members located at each longitudinal end of the reinforcing member and having a plurality of struts situated parallel to the central axis and connected to the joint members and a plurality of connecting portions, each connecting portion connecting a pair of struts situated adjacent to each other.

3. An expandable tubular reinforcing member according to claim 2, wherein each connecting portion has a thickness less than that of each strut so that when the reinforcing member is expanded, each connecting portion is expanded.

4. An expandable tubular reinforcing member according to claim 2, wherein each strut has a length shorter than a length of each elongated member so that when the reinforcing member is expanded, the struts are equally bent at both ends simultaneously.

5. An expandable tubular reinforcing member according to claim 1, wherein said each joint member includes two side portions and one middle portion for joining the two side portions, two elongated members in one row of the elongated members being connected to one side portion of one joint member in one row of the joint members and to respective side portions of two joint members in another row of the joint members, respectively.

6. An expandable tubular reinforcing member according to claim 5, wherein said middle portion is located at ends of the two side portions to have an open side in the joint member, open sides in one row of the joint members being oriented in a same direction and directed in an opposite direction relative to open sides in an adjacent row of the joint members.

7. An expandable tubular reinforcing member according to claim 6, wherein said elongated members have first and second elongated members alternately arranged to each other in one row of the elongated members, each first elongated member being connected to the side portion near the open side and each second elongated member being connected to the side portion near the middle portion so that when the reinforcing member is expanded, the first elongated members are bent first.

8. An expandable tubular reinforcing member according to claim 7, wherein the elongated members are integrally formed with the joint members and the end portions.

9. An expandable tubular reinforcing member according to claim 8, wherein said each joint member has a C shape, and a thickness of each joint member is less than that of each elongated member.

10. An expandable tubular reinforcing member according to claim 1, wherein said reinforcing member is coated with a substance which prevents blood coagulation.

11. An expandable tubular reinforcing member according to claim 1, wherein said reinforcing member is coated with a bio-absorbable material.

12. An expandable tubular reinforcing member according to claim 1, wherein said reinforcing member is formed of a radioactive material.

13. An expandable tubular reinforcing member according to claim 1, wherein said reinforcing member is formed of stainless steel.

14. An expandable tubular reinforcing member according to claim 1, wherein said reinforcing member is formed of a NiTi alloy.

15. An expandable tubular reinforcing member according to claim 1, wherein the reinforcing member has a porous surface so that a drug can be retained on the surface.

16. An expandable tubular reinforcing member used for a body lumen comprising, a plurality of rows of expandable joint members, each of the rows being spaced for a predetermined distance away from each other along a longitudinal central axis of the reinforcing member, each row being formed of a plurality of said joint members spaced apart from each other and arranged circularly around the central axis with a first diameter, a plurality of rows of flexible elongated members, each of the rows being situated between adjacent two rows of the joint members, said elongated members extending diagonally to the central axis of the reinforcing member, each of said elongated members connecting two of the joint members situated in adjacent two rows of the joint members so that when a radial force is applied from an inside of the reinforcing member, the elongated members are pivoted relative to the joint members to thereby allow the reinforcing member to have a second diameter larger than the first diameter, and two rows of end portions disposed parallel to the rows of the joint members, each of the rows of the end portions being connected to a row of the joint members located at each longitudinal end of the reinforcing member and having a plurality of struts situated parallel to the central axis and connected to the joint members and a plurality of connecting portions, each connecting portion connecting a pair of struts situated adjacent to each other and having a thickness less than that of each strut so that when the reinforcing member is expanded, each connecting portion is pivoted.

17. An expandable tubular reinforcing member used for a body lumen comprising, a plurality of rows of expandable joint members, each of the rows being spaced for a predetermined distance away from each other along a longitudinal central axis of the reinforcing member, each row being formed of a plurality of said joint members spaced apart from each other and arranged circularly around the central axis with a first diameter, each joint member including two side portions and one middle portion for joining the two side portions, said middle portion being located at ends of the two side portions to have an open side in the joint member, open sides in one row of the joint members being oriented in a same direction and directed in an opposite direction relative to open sides in an adjacent row of the joint members, and a plurality of rows of flexible elongated members, each of the rows being situated between adjacent two rows of the joint members, said elongated members extending diagonally to the central axis of the reinforcing member, two elongated members in one row of the elongated members being connected to one side portion of one joint member in one row of the joint members and to respective side portions of two joint members in another row of the joint members, respectively, so that when a radial force is applied from an inside of the reinforcing member, the elongated members are pivoted relative to the joint members to thereby allow the reinforcing member to have a second diameter larger than the first diameter, said elongated members having first and second elongated members alternately arranged to each other in one row of the elongated members, each first elongated member being connected to the side portion near the open side and each second elongated member being connected to the side portion near the middle portion so that when the reinforcing member is expanded, the first elongated members are pivoted first.

18. An expandable tubular reinforcing member according to claim 1, wherein said elongated members in each row extend substantially parallel to each other.

* * * * *